United States Patent [19]

Bishop et al.

[11] Patent Number: 4,561,439
[45] Date of Patent: Dec. 31, 1985

[54] THROMBECTOMY CATHETER

[75] Inventors: David C. Bishop, Shoreham-by-Sea; Gordon L. Lawrence, Arundel, both of England

[73] Assignee: Matburn (Holdings) Limited, London, England

[21] Appl. No.: 463,910

[22] Filed: Feb. 4, 1983

[30] Foreign Application Priority Data

Feb. 5, 1982 [GB] United Kingdom ............... 8203304

[51] Int. Cl.$^4$ ............................................ A61M 25/00
[52] U.S. Cl. .................... 128/348.1; 128/344; 604/103
[58] Field of Search ............... 128/348.1, 344; 604/96, 604/103

[56] References Cited

U.S. PATENT DOCUMENTS 3,467,101 9/1969 Fogarty et al. ............... 128/348.1
4,276,874 7/1981 Wolvek et al. ..................... 604/96
4,351,341 9/1982 Goldberg et al. ............... 604/97 X
4,444,188 4/1984 Bazell et al. ..................... 128/348.1

Primary Examiner—Stephen C. Pellegrino
Attorney, Agent, or Firm—McAulay, Fields, Fisher, Goldstein & Nissen

[57] ABSTRACT

A tubular surgical instrument such as a thrombectomy catheter or gall stone dislodger comprises a shaft of plastics material with a coiled spring projecting from its forward end. A portion of the spring is secured in a coupling portion at the distal end of the shaft. The coupling portion has an outer surface with a recess which flares forwards from a shoulder of the shaft towards an annular support surface. The spring is secured in the coupling portion. A balloon is inflatable by fluid pressure applied through a lumen in the shaft. An end of the balloon is located in the recess and is secured by a tie. The balloon is secured directly or indirectly to the spring by a second tie forward of the first. The instruments are primarily intended for use as aortic or venous catheters and especially thrombectomy catheters, but can also be used for example as gall stone dislodgers.

7 Claims, 2 Drawing Figures

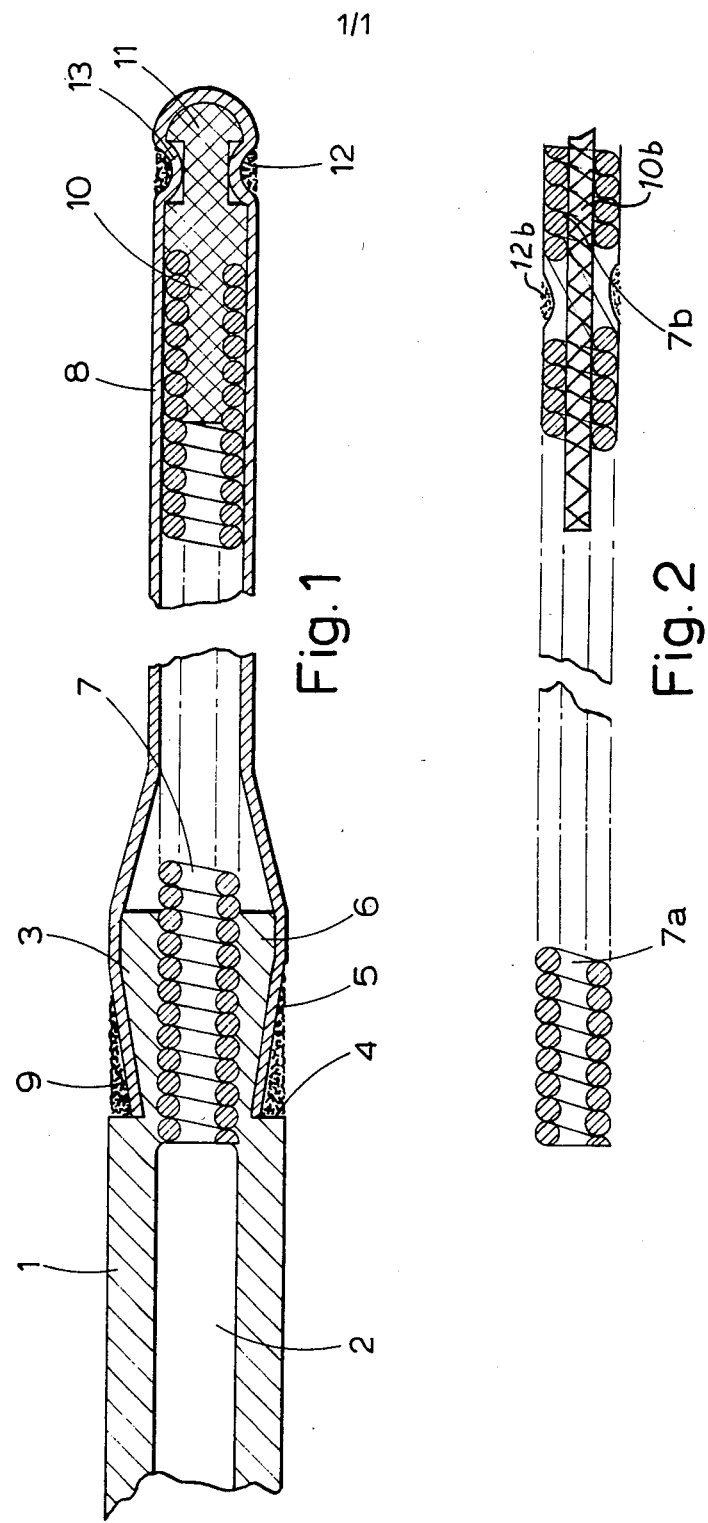

THROMBECTOMY CATHETER

BACKGROUND TO THE INVENTION

Thrombectomy catheters usually comprise a catheter tube. The tube is commonly called a "shaft" and the passage inside the tube is commonly called the "lumen". A thrombectomy catheter usually has at its distal end a coiled spring which is secured in and projects forwards of the distal end of the shaft. This spring is enclosed in an inflatable balloon which is secured to the shaft near its distal end. Thus, the spring and the balloon form a flexible tip of the catheter. When the catheter is in use, the balloon can be inflated by the pressure of fluid transmitted to the interior of the balloon through the lumen.

An object of the present invention is to provide a thrombectomy catheter or similar tubular surgical instrument with an improved tip. Another object is to provide a thrombectomy catheter with which the inflatable balloon is secured to the shaft with greater security than is provided in existing such catheters.

BRIEF SUMMARY OF THE INVENTION

The invention provides a tubular surgical instrument with a flexible distal end portion, the said instrument comprising a shaft which has a lumen therein, a coiled spring projecting from a distal end of the shaft, a coupling portion at the distal end of the shaft, a portion of the spring being secured in the coupling portion and a balloon which is inflatable by fluid pressure applied through the lumen, and which is secured directly or indirectly to the spring.

The instrument may be a thrombectomy catheter or other instrument such as a gall stone dislodger.

The shaft may be of polyvinylchloride or other suitable plastics or woven material and the balloon may be of latex.

If the balloon is secured indirectly to the spring, it may be secured to a plug, preferably of polyethylene but if desired of nylon, or similar material, projecting from the distal end of the spring. The plug is secured in the spring with an epoxy adhesive or, preferably, is formed in situ in which case no adhesive is required. If the balloon is secured directly to the spring, the spring may have a second portion spaced from, but secured to, the distal end of the first porton of the spring and filled with solder or other means such as for example epoxy resin. The second tie is then located in the space between the two portions of spring.

BRIEF DESCRIPTION OF THE ACCOMPANYING DRAWINGS

FIG. 1 is a sectional view of a distal end portion of a thrombectomy catheter, and FIG. 2 is a view, partly in section, of a spring forming part of an alternative thrombectomy catheter.

DESCRIPTION OF PREFERRED EMBODIMENTS

In the embodiment of the invention illustrated in the drawings, a thrombectomy catheter comprises a shaft 1 of extruded polyvinylchloride (PVC) or other suitable plastics material. The shaft has a lumen 2. The distal end of the shaft 1 has an integral coupling portion 3. To provide this coupling portion, the distal end of the shaft has a portion of reduced external diameter which provides a shoulder 4 from which the outer surface of the shaft flares in the forward direction to provide a recess 5 leading to an annular support portion 6. The external diameter of the portion 6 is less than that of the main portion of the shaft.

A coiled metal spring 7 projects forwards of the coupling portion 3, the material of the coupling portion of the shaft being moulded or formed into the rear end of the spring 7 by any suitable form of heating. The heating is preferably radio-frequency (dielectric) heating or it can be ultrasonic heating or any other suitable form of heating. The operation of securing the spring 7 in the coupling portion 3 also forms the flared recess 5.

The spring 7 is enclosed in a balloon 8 which is conveniently of latex. This balloon may be inflated by fluid pressure applied through the lumen 2 to the interior of the balloon 8. The end of the balloon 8 is located in the flared recess 5 and is secured therein by a first tie 9 of thread which is conveniently thread made of polyester material or that known under the Registered Trade Mark "Terylene". The relative sizes of the flared recess 5 and the annular support portion 6 as well as the thickness of the balloon are such that when the join is completed, the outer surface of the shaft 5, the tie 9 and the portion of the balloon over the annular support 6 are flush with each other.

This join gives greater security of attachment of the balloon to the shaft than is provided in known thrombectomy catheters.

In the embodiment illustrated in FIG. 1 a moulded plug 10 which is conveniently of polyethylene or nylon, is secured in the distal end of the spring 7. This plug 10 has a mushroom head 11. The balloon 8 has a closed end which fits over the mushroom head of the plug and is secured to the plug by a second tie 12 of thread of the same material as the first tie 9. The tie 12 is secured in an annular recess 13 behind the mushroom head 11 as shown in the drawing.

In an alternative construction illustrated in FIG. 2, the spring 7 is not fitted with a plug 10 but is constructed in a proximal portion 7a and a distal portion 7b which portions are spaced from each other.

The distal portion 7b is filled with a suitable solder or other filler material such as, for example, epoxy resin and this filler material 10b extends into part of the proximal portion. The balloon encloses the spring in a similar way to the embodiment shown in FIG. 1, the portion 7b of the spring performing a function analogous to that of the mushroom head 11 of the plug illustrated in FIG. 1. The forward portion of the balloon is secured to the distal portion of the spring by a tie 12b secured in the space between the spring portion 7a and 7b.

Although the invention has been described as applied to a thrombectomy catheter, it can be used in other tubular surgical instruments such as gall stone dislodgers.

What is claimed is:

1. A tubular surgical instrument with a flexible distal end portion, the said instrument comprising a shaft which has a lumen therein, a coiled spring projecting from a distal end of the shaft, a coupling portion at the distal end of the shaft, a portion of the spring being secured in the coupling portion and a balloon, which is inflatable by fluid pressure, applied through the lumen secured to the spring, said coupling portion having a recess, a shoulder and an annular support surface; the outer surface of said recess flaring forwardly from said shoulder of said shaft towards said annular support surface; an end of the balloon being received in said recess; a first tie securing said balloon in said recess; and a second tie securing said balloon to said spring and being located forwardly of said first tie.

2. A surgical instrument as claimed in claim 1, wherein one end of the spring is secured in the coupling portion and a plug is secured in the other end of the spring, the plug having a mushroom head behind which is an annular recess and wherein the balloon is fitted over the plug and is secured to the plug by a tie in the annular recess.

3. A surgical instrument as claimed in claim 2 wherein the plug is of polyethylene.

4. A surgical instrument as claimed in claim 1, wherein the outer surfaces of the shaft, the first tie and the portion of the balloon extending over the annular support surface are flush with each other.

5. A tubular surgical instrument with a flexible distal end portion, the said instrument comprising a shaft which has a lumen therein, a coiled spring projecting from the distal end of the shaft, a coupling portion at the distal end of the shaft, a portion of the spring being secured in the coupling portion, and a balloon, which is inflatable by fluid pressure applied through the lumen, secured to said spring, said spring comprising proximal and distal portions which are spaced from each other, and a filler material is provided in the distal portion and extends into part of the proximal portion, the balloon being fitted over and directly contacting the spring and being secured to the spring by a tie between the two portions of the spring.

6. A surgical instrument as claimed in claim 5 in which the shaft is of plastics material.

7. A surgical instrument as claimed in claim 6 in which the shaft is of polyvinylchloride.

* * * * *